(12) United States Patent
Eberhardt et al.

(10) Patent No.: US 11,607,311 B2
(45) Date of Patent: Mar. 21, 2023

(54) STENTS FOR PROSTHETIC HEART VALVES

(71) Applicant: Medtronic, Inc., Minneapolis, MN (US)

(72) Inventors: Carol E. Eberhardt, Fullerton, CA (US); Charles P. Tabor, St. Cloud, MN (US); Carolyn Majkrzak, Chanhassen, MN (US); Timothy R. Ryan, Minnetrista, MN (US); Melissa Young, Cleveland Heights, OH (US); Maria Awad, Irvine, CA (US); Janice L. Shay, Lake Forest, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/359,340

(22) Filed: Jun. 25, 2021

(65) Prior Publication Data
US 2021/0322161 A1   Oct. 21, 2021

Related U.S. Application Data

(63) Continuation of application No. 16/932,779, filed on Jul. 19, 2020, which is a continuation of application
(Continued)

(51) Int. Cl.
*A61F 2/24* (2006.01)
*A61F 2/82* (2013.01)
(Continued)

(52) U.S. Cl.
CPC ............ *A61F 2/2418* (2013.01); *A61F 2/013* (2013.01); *A61F 2/07* (2013.01); *A61F 2/243* (2013.01);
(Continued)

(58) Field of Classification Search
CPC ........ A61F 2/24; A61F 2/2409; A61F 2/2418; A61F 2/82; A61F 2/06; A61F 2/07;
(Continued)

(56) References Cited

U.S. PATENT DOCUMENTS

| 3,334,629 A | 8/1967 | Cohn |
| 3,409,013 A | 11/1968 | Berry |

(Continued)

FOREIGN PATENT DOCUMENTS

| CN | 2007-100074433 | 8/2007 |
| DE | 195 46 692 A1 | 6/1997 |

(Continued)

OTHER PUBLICATIONS

Andersen, H.R. etal, "Transluminal implantation of artificial heart valves. Description of a new expandable aortic valve and initial results with implantation by catheter technique in closed chest pigs." Euro. Heart J. (1992) 13:704-708.
(Continued)

*Primary Examiner* — Seema Mathew
(74) *Attorney, Agent, or Firm* — Medler Ferro Woodhouse & Mills PLLC

(57) ABSTRACT

A stented valve including a stent structure including a generally tubular body portion having a first end, a second end, an interior area, a longitudinal axis, and a plurality of vertical wires extending generally parallel to the longitudinal axis around a periphery of the body portion, wherein the plurality of vertical wires includes multiple commissure wires and at least one structural wire positioned between adjacent commissure wires, and a plurality of V-shaped wire structures having a first end, a second end, and a peak between the first and second ends, wherein a first end of each V-shaped structure extends from a first vertical wire and a second end of each V-shaped structure extends from a
(Continued)

second vertical wire that is adjacent to the first vertical wire, wherein each V-shaped structure is oriented so that its peak is facing in the same direction relative to the first and second ends of the body portion, and a valve structure including a plurality of leaflets attached to the stent structure within the tubular body portion.

9 Claims, 9 Drawing Sheets

Related U.S. Application Data

No. 15/099,075, filed on Apr. 14, 2016, now Pat. No. 10,758,343, which is a continuation of application No. 14/087,990, filed on Nov. 22, 2013, now Pat. No. 9,333,100, which is a continuation of application No. 12/358,980, filed on Jan. 23, 2009, now Pat. No. 8,628,566.

(60) Provisional application No. 61/062,207, filed on Jan. 24, 2008.

(51) Int. Cl.
*A61F 2/01* (2006.01)
*A61F 2/07* (2013.01)
*A61F 2/95* (2013.01)
*A61F 2/89* (2013.01)
*A61F 2/90* (2013.01)
*A61F 2/915* (2013.01)

(52) U.S. Cl.
CPC .......... *A61F 2/2403* (2013.01); *A61F 2/2412* (2013.01); *A61F 2/2436* (2013.01); *A61F 2/2439* (2013.01); *A61F 2/82* (2013.01); *A61F 2/2433* (2013.01); *A61F 2/89* (2013.01); *A61F 2/90* (2013.01); *A61F 2/915* (2013.01); *A61F 2002/016* (2013.01); *A61F 2002/9505* (2013.01); *A61F 2002/9511* (2013.01); *A61F 2220/0058* (2013.01); *A61F 2220/0075* (2013.01); *A61F 2220/0091* (2013.01); *A61F 2230/0006* (2013.01); *A61F 2230/008* (2013.01); *A61F 2230/0054* (2013.01); *A61F 2250/003* (2013.01); *A61F 2250/0018* (2013.01); *A61F 2250/0039* (2013.01); *A61F 2250/0098* (2013.01)

(58) Field of Classification Search
CPC ...... A61F 2/2403; A61F 2/243; A61F 2/2436; A61F 2/90
See application file for complete search history.

(56) References Cited

U.S. PATENT DOCUMENTS

| | | | |
|---|---|---|---|
| 3,540,431 | A | 11/1970 | Mobin-Uddin |
| 3,587,115 | A | 6/1971 | Shiley |
| 3,628,535 | A | 12/1971 | Ostrowsky et al. |
| 3,642,004 | A | 2/1972 | Osthagen et al. |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,233,690 | A | 11/1980 | Akins |
| 4,265,694 | A | 5/1981 | Boretos |
| 4,291,420 | A | 9/1981 | Reul |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,388,735 | A | 6/1983 | Ionescu et al. |
| 4,425,908 | A | 1/1984 | Simon |
| 4,470,157 | A | 9/1984 | Love |
| 4,501,030 | A | 2/1985 | Lane |
| 4,506,394 | A | 3/1985 | Debard |
| 4,574,803 | A | 3/1986 | Storz |
| 4,580,568 | A | 4/1986 | Gianturco |
| 4,592,340 | A | 6/1986 | Boyles |
| 4,610,688 | A | 9/1986 | Silvestrini et al. |
| 4,612,011 | A | 9/1986 | Kautzky |
| 4,647,283 | A | 3/1987 | Carpentier et al. |
| 4,648,881 | A | 3/1987 | Carpentier et al. |
| 4,655,771 | A | 4/1987 | Wallsten |
| 4,662,885 | A | 5/1987 | DiPisa, Jr. |
| 4,665,906 | A | 5/1987 | Jervis |
| 4,681,908 | A | 7/1987 | Broderick et al. |
| 4,710,192 | A | 12/1987 | Liotta et al. |
| 4,733,665 | A | 3/1988 | Palmaz |
| 4,777,951 | A | 10/1988 | Cribier et al. |
| 4,787,899 | A | 11/1988 | Lazarus |
| 4,796,629 | A | 1/1989 | Grayzel |
| 4,797,901 | A | 1/1989 | Goerne et al. |
| 4,819,751 | A | 4/1989 | Shimada et al. |
| 4,834,755 | A | 5/1989 | Silvestrini et al. |
| 4,846,830 | A | 7/1989 | Knoch et al. |
| 4,856,516 | A | 8/1989 | Hillstead |
| 4,872,874 | A | 10/1989 | Taheri |
| 4,878,495 | A | 11/1989 | Grayzel |
| 4,878,906 | A | 11/1989 | Lindemann et al. |
| 4,883,458 | A | 11/1989 | Shiber |
| 4,909,252 | A | 3/1990 | Goldberger |
| 4,913,141 | A | 4/1990 | Hillstead |
| 4,917,102 | A | 4/1990 | Miller et al. |
| 4,922,905 | A | 5/1990 | Strecker |
| 4,954,126 | A | 9/1990 | Wallsten |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,002,559 | A | 3/1991 | Tower |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,061,273 | A | 10/1991 | Yock |
| 5,085,635 | A | 2/1992 | Cragg |
| 5,089,015 | A | 2/1992 | Ross |
| 5,104,399 | A | 4/1992 | Lazarus |
| 5,108,425 | A | 4/1992 | Hwang |
| 5,152,771 | A | 10/1992 | Sabbaghian et al. |
| 5,161,547 | A | 11/1992 | Tower |
| 5,163,953 | A | 11/1992 | Vince |
| 5,167,628 | A | 12/1992 | Boyles |
| 5,201,757 | A | 4/1993 | Heyn et al. |
| 5,217,483 | A | 6/1993 | Tower |
| 5,232,445 | A | 8/1993 | Bonzel |
| 5,272,909 | A | 12/1993 | Nguyen et al. |
| 5,295,958 | A | 3/1994 | Shturman |
| 5,327,774 | A | 7/1994 | Nguyen et al. |
| 5,332,402 | A | 7/1994 | Teitelbaum et al. |
| 5,350,398 | A | 9/1994 | Pavcnik et al. |
| 5,354,330 | A | 10/1994 | Hanson et al. |
| 5,370,685 | A | 12/1994 | Stevens |
| 5,389,106 | A | 2/1995 | Tower |
| 5,397,351 | A | 3/1995 | Pavcnik et al. |
| 5,397,355 | A | 3/1995 | Marin et al. |
| 5,411,552 | A | 5/1995 | Andersen et al. |
| 5,415,633 | A | 5/1995 | Lazarus et al. |
| 5,431,676 | A | 7/1995 | Dubrul et al. |

(56) References Cited

U.S. PATENT DOCUMENTS

| | | |
|---|---|---|
| 5,433,723 A | 7/1995 | Lindenberg et al. |
| 5,443,446 A | 8/1995 | Shturman |
| 5,443,500 A | 8/1995 | Sigwart |
| 5,449,384 A | 9/1995 | Johnson |
| 5,480,423 A | 1/1996 | Ravenscroft et al. |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,720,776 A | 2/1998 | Chuter et al. |
| 5,746,709 A | 5/1998 | Rom et al. |
| 5,749,890 A | 5/1998 | Shaknovich |
| 5,749,921 A | 5/1998 | Lenker et al. |
| 5,766,151 A | 6/1998 | Valley et al. |
| 5,776,142 A | 7/1998 | Gunderson |
| 5,782,809 A | 7/1998 | Umeno et al. |
| 5,800,455 A | 9/1998 | Palarmo et al. |
| 5,800,456 A | 9/1998 | Maeda et al. |
| 5,800,508 A | 9/1998 | Goicoechea et al. |
| 5,807,405 A | 9/1998 | Vanney et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Anderson et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,891,191 A | 4/1999 | Stinson |
| 5,906,619 A | 5/1999 | Olson et al. |
| 5,907,893 A | 6/1999 | Zadno-Azizi et al. |
| 5,908,452 A | 6/1999 | Bokros et al. |
| 5,913,842 A | 6/1999 | Boyd et al. |
| 5,925,063 A | 7/1999 | Khosravi |
| 5,944,738 A | 8/1999 | Amplatz et al. |
| 5,944,750 A | 8/1999 | Tanner et al. |
| 5,954,766 A | 9/1999 | Zadno-Azizi et al. |
| 5,957,949 A | 9/1999 | Leonhardt et al. |
| 5,964,405 A | 10/1999 | Benary et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,126,685 A | 1/2000 | Lenker et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,076,742 A | 6/2000 | Benary |
| 6,077,297 A | 6/2000 | Robinson et al. |
| 6,091,042 A | 7/2000 | Benary |
| 6,102,944 A | 8/2000 | Huynh et al. |
| 6,110,201 A | 8/2000 | Quijano et al. |
| 6,113,612 A | 9/2000 | Swanson et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Anderson et al. |
| 6,168,616 B1 | 1/2001 | Brown, III |
| 6,168,618 B1 | 1/2001 | Frantzen |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,214,036 B1 | 4/2001 | Letendre et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,267,783 B1 | 7/2001 | Lentendre et al. |
| 6,277,555 B1 | 8/2001 | Duran et al. |
| 6,287,339 B1 | 9/2001 | Vasquez et al. |
| 6,296,662 B1 | 10/2001 | Caffey |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,346,118 B1 | 2/2002 | Baker et al. |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,979 B1 | 4/2002 | Beyar et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 * | 7/2002 | Garrison ............... A61F 2/2436 623/2.11 |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,517,548 B2 | 2/2003 | Lorentzen et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| RE38,091 E | 4/2003 | Strecker |
| 6,558,418 B2 | 5/2003 | Capentier et al. |
| 6,562,031 B2 | 5/2003 | Chandrasekaran et al. |
| 6,562,058 B2 | 5/2003 | Seguin et al. |
| 6,562,063 B1 | 5/2003 | Euteneur et al. |
| 6,569,196 B1 | 5/2003 | Vesely |
| 6,582,460 B1 | 6/2003 | Cryer |
| 6,582,462 B1 | 6/2003 | Andersen et al. |
| 6,585,758 B1 | 7/2003 | Chouinard et al. |
| 6,592,546 B1 | 7/2003 | Barbut et al. |

(56) References Cited

U.S. PATENT DOCUMENTS

| | | |
|---|---|---|
| 6,600,803 B2 | 7/2003 | Bruder |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,085 B1 | 10/2003 | Caffey et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,666,881 B1 | 12/2003 | Richter et al. |
| 6,669,724 B2 | 12/2003 | Park et al. |
| 6,673,089 B1 | 1/2004 | Yassour et al. |
| 6,673,106 B2 | 1/2004 | Mitelberg et al. |
| 6,676,698 B2 | 1/2004 | McGuckin, Jr. et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,121 B2 | 5/2004 | Beyersdorf et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,767,362 B2 | 7/2004 | Schreck |
| 6,769,434 B2 | 8/2004 | Liddicoat et al. |
| 6,776,791 B1 | 8/2004 | Stallings et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,849,084 B2 | 2/2005 | Rabkin et al. |
| 6,866,650 B2 | 3/2005 | Stevens |
| 6,866,669 B2 | 3/2005 | Buzzard et al. |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,018,406 B2 | 3/2006 | Seguin et al. |
| 7,022,132 B2 | 4/2006 | Kocur |
| 7,025,780 B2 | 4/2006 | Gabbay |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,137,184 B2 | 11/2006 | Schreck |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,680 B2 | 8/2007 | Freitag |
| 7,252,682 B2 | 8/2007 | Seguin |
| 7,261,732 B2 | 8/2007 | Justino |
| 7,267,686 B2 | 9/2007 | Dimatteo et al. |
| 7,300,457 B2 | 11/2007 | Palmaz |
| 7,300,463 B2 | 11/2007 | Liddicoat |
| 7,311,730 B2 | 12/2007 | Gabbay |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,399,315 B2 | 7/2008 | Iobbi |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,473,271 B2 | 1/2009 | Gunderson |
| 7,481,838 B2 | 1/2009 | Carpentier et al. |
| 7,510,575 B2 | 5/2009 | Spenser et al. |
| 7,544,206 B2 | 6/2009 | Cohn et al. |
| 7,547,322 B2 | 6/2009 | Sarac et al. |
| 7,556,386 B2 | 7/2009 | Smith |
| 7,556,646 B2 | 7/2009 | Yang et al. |
| 7,569,071 B2 | 8/2009 | Haverkost et al. |
| 7,618,446 B2 | 11/2009 | Andersen et al. |
| 7,618,447 B2 | 11/2009 | Case et al. |
| 7,635,386 B1 | 12/2009 | Gammie |
| 7,651,521 B2 | 1/2010 | Ton et al. |
| 7,682,390 B2 | 3/2010 | Seguin |
| 7,708,775 B2 | 5/2010 | Rowe et al. |
| 7,722,666 B2 | 5/2010 | Lafontaine |
| 7,748,389 B2 | 7/2010 | Salahieh et al. |
| 7,771,463 B2 | 8/2010 | Ton et al. |
| 7,780,726 B2 | 8/2010 | Seguin |
| 7,785,361 B2 | 8/2010 | Nikolchev et al. |
| 7,806,726 B2 | 8/2010 | Seguin |
| 7,803,177 B2 | 9/2010 | Hartley et al. |
| 7,837,643 B2 | 11/2010 | Levine et al. |
| 7,857,845 B2 | 12/2010 | Stacchino et al. |
| 7,862,602 B2 | 1/2011 | Licata et al. |
| 7,947,075 B2 | 5/2011 | Goetz et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,993,394 B2 | 8/2011 | Hariton et al. |
| 8,025,750 B2 | 11/2011 | Tuval et al. |
| 8,052,750 B2 | 11/2011 | Tuval et al. |
| 8,075,611 B2 | 12/2011 | Millwee et al. |
| 8,133,270 B2 | 3/2012 | Kheradvar et al. |
| 8,137,398 B2 | 3/2012 | Tuval et al. |
| 8,236,045 B2 | 8/2012 | Benichou et al. |
| 8,252,052 B2 | 8/2012 | Salahieh et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,398,704 B2 | 3/2013 | Straubinger |
| 8,403,983 B2 * | 3/2013 | Quadri ............... A61F 2/2412 623/2.14 |
| 8,414,643 B2 | 4/2013 | Tuval et al. |

(56) References Cited

U.S. PATENT DOCUMENTS

| | | | |
|---|---|---|---|
| 8,454,685 B2 | 6/2013 | Hariton et al. | |
| 8,460,366 B2 | 6/2013 | Rowe | |
| 8,465,540 B2 | 6/2013 | Straubinger et al. | |
| 8,585,755 B2 * | 11/2013 | Chau | A61F 2/24 623/2.18 |
| 8,603,160 B2 | 12/2013 | Salahieh et al. | |
| 8,628,566 B2 | 1/2014 | Eberhardt | |
| 8,652,202 B2 | 2/2014 | Alon et al. | |
| 8,673,000 B2 | 3/2014 | Tabor et al. | |
| 8,685,086 B2 * | 4/2014 | Navia | A61F 2/2418 623/2.14 |
| 8,696,743 B2 * | 4/2014 | Holecek | A61F 2/2412 623/2.12 |
| 8,702,788 B2 | 4/2014 | Kheradvar et al. | |
| 8,828,078 B2 | 9/2014 | Salahieh et al. | |
| 8,840,663 B2 | 9/2014 | Salahieh et al. | |
| 9,132,024 B2 | 9/2015 | Brinser | |
| 9,168,131 B2 | 10/2015 | Yohanan et al. | |
| 9,339,382 B2 | 5/2016 | Tabor et al. | |
| 9,393,110 B2 | 7/2016 | Levi et al. | |
| 9,393,115 B2 | 7/2016 | Tabor et al. | |
| 9,615,921 B2 * | 4/2017 | Alkhatib | A61F 2/2412 |
| 10,016,274 B2 | 7/2018 | Tabor et al. | |
| 11,058,535 B2 * | 7/2021 | Noe | A61F 2/2418 |
| 2001/0001314 A1 | 5/2001 | Davison et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0011189 A1 | 8/2001 | Drasler et al. | |
| 2001/0021872 A1 | 9/2001 | Bailey et al. | |
| 2001/0025196 A1 | 9/2001 | Chinn et al. | |
| 2001/0032013 A1 | 10/2001 | Marton | |
| 2001/0037142 A1 | 11/2001 | Stelter et al. | |
| 2001/0039450 A1 | 11/2001 | Pavcnik et al. | |
| 2001/0041928 A1 | 11/2001 | Pavcnik et al. | |
| 2001/0044647 A1 | 11/2001 | Pinchuk et al. | |
| 2001/0047150 A1 | 11/2001 | Chobotov | |
| 2001/0049550 A1 | 12/2001 | Martin et al. | |
| 2002/0010508 A1 | 1/2002 | Chobotov | |
| 2002/0026233 A1 | 2/2002 | Shaknovich | |
| 2002/0029014 A1 | 3/2002 | Jayaraman | |
| 2002/0032480 A1 | 3/2002 | Spence et al. | |
| 2002/0032481 A1 | 3/2002 | Gabbay | |
| 2002/0035396 A1 | 3/2002 | Heath | |
| 2002/0042650 A1 | 4/2002 | Vardi et al. | |
| 2002/0052651 A1 | 5/2002 | Myers et al. | |
| 2002/0058995 A1 | 5/2002 | Stevens | |
| 2002/0065545 A1 | 5/2002 | Leonhardt et al. | |
| 2002/0072789 A1 | 6/2002 | Hackett et al. | |
| 2002/0077696 A1 | 6/2002 | Zadno-Azizi et al. | |
| 2002/0091439 A1 | 7/2002 | Baker et al. | |
| 2002/0095209 A1 | 7/2002 | Zadno-Azizi et al. | |
| 2002/0099439 A1 | 7/2002 | Schwartz et al. | |
| 2002/0103533 A1 | 8/2002 | Langberg et al. | |
| 2002/0107565 A1 | 8/2002 | Greenhalgh | |
| 2002/0111674 A1 | 8/2002 | Chouinard et al. | |
| 2002/0120277 A1 | 8/2002 | Hauschild et al. | |
| 2002/0120323 A1 | 8/2002 | Thompson et al. | |
| 2002/0123802 A1 | 9/2002 | Snyders | |
| 2002/0133183 A1 | 9/2002 | Lentz et al. | |
| 2002/0138138 A1 | 9/2002 | Yang | |
| 2002/0151970 A1 | 10/2002 | Garrison et al. | |
| 2002/0161392 A1 | 10/2002 | Dubrul | |
| 2002/0161394 A1 | 10/2002 | Macoviak et al. | |
| 2002/0186558 A1 | 12/2002 | Plank et al. | |
| 2002/0188341 A1 | 12/2002 | Elliott | |
| 2002/0193871 A1 | 12/2002 | Beyersdorf et al. | |
| 2003/0004560 A1 | 1/2003 | Chobotov et al. | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0028247 A1 | 2/2003 | Cali | |
| 2003/0036791 A1 | 2/2003 | Phillip et al. | |
| 2003/0040771 A1 | 2/2003 | Hyodoh et al. | |
| 2003/0040772 A1 | 2/2003 | Hyodoh et al. | |
| 2003/0040792 A1 | 2/2003 | Gabbay | |
| 2003/0050684 A1 | 3/2003 | Abrams et al. | |
| 2003/0050694 A1 | 3/2003 | Yang et al. | |
| 2003/0055495 A1 | 3/2003 | Pease et al. | |
| 2003/0065386 A1 | 4/2003 | Weadock | |
| 2003/0069492 A1 | 4/2003 | Abrams et al. | |
| 2003/0109924 A1 | 6/2003 | Cribier | |
| 2003/0114913 A1 * | 6/2003 | Spenser | A61F 2/2412 623/1.11 |
| 2003/0125795 A1 | 7/2003 | Pavcnik et al. | |
| 2003/0130726 A1 | 7/2003 | Thorpe et al. | |
| 2003/0130727 A1 | 7/2003 | Drasler et al. | |
| 2003/0130729 A1 | 7/2003 | Paniagua et al. | |
| 2003/0135257 A1 | 7/2003 | Taheri | |
| 2003/0139804 A1 | 7/2003 | Hankh et al. | |
| 2003/0149475 A1 | 8/2003 | Hyodoh et al. | |
| 2003/0149476 A1 | 8/2003 | Damm et al. | |
| 2003/0149478 A1 | 8/2003 | Figulla et al. | |
| 2003/0153974 A1 | 8/2003 | Spenser et al. | |
| 2003/0158595 A1 | 8/2003 | Randall et al. | |
| 2003/0171805 A1 | 9/2003 | Berg | |
| 2003/0176914 A1 | 9/2003 | Rabkin et al. | |
| 2003/0181850 A1 | 9/2003 | Diamond et al. | |
| 2003/0191519 A1 | 10/2003 | Lombardi et al. | |
| 2003/0199913 A1 | 10/2003 | Dubrul et al. | |
| 2003/0199963 A1 | 10/2003 | Tower et al. | |
| 2003/0199971 A1 | 10/2003 | Tower et al. | |
| 2003/0199972 A1 | 10/2003 | Paniagua et al. | |
| 2003/0199975 A1 | 10/2003 | Gabbay | |
| 2003/0212410 A1 | 11/2003 | Stenzel et al. | |
| 2003/0212452 A1 | 11/2003 | Zadno-Azizi et al. | |
| 2003/0212454 A1 | 11/2003 | Scott et al. | |
| 2003/0225445 A1 | 12/2003 | Derus et al. | |
| 2003/0233140 A1 | 12/2003 | Hartley et al. | |
| 2003/0236568 A1 | 12/2003 | Hojeibane et al. | |
| 2004/0034411 A1 | 2/2004 | Quijano et al. | |
| 2004/0039436 A1 * | 2/2004 | Spenser | A61F 2/2436 623/2.14 |
| 2004/0044402 A1 | 3/2004 | Jung et al. | |
| 2004/0049207 A1 | 3/2004 | Goldfarb et al. | |
| 2004/0049224 A1 | 3/2004 | Buehlmann et al. | |
| 2004/0049262 A1 | 3/2004 | Obermiller et al. | |
| 2004/0049266 A1 | 3/2004 | Anduiza et al. | |
| 2004/0059429 A1 | 3/2004 | Amin et al. | |
| 2004/0082904 A1 | 4/2004 | Houde et al. | |
| 2004/0082989 A1 | 4/2004 | Cook et al. | |
| 2004/0088045 A1 | 5/2004 | Cox | |
| 2004/0092858 A1 | 5/2004 | Wilson et al. | |
| 2004/0092989 A1 | 5/2004 | Wilson et al. | |
| 2004/0093005 A1 | 5/2004 | Durcan | |
| 2004/0093060 A1 | 5/2004 | Sequin et al. | |
| 2004/0093063 A1 | 5/2004 | Wright et al. | |
| 2004/0093070 A1 | 5/2004 | Hojeibane et al. | |
| 2004/0093075 A1 | 5/2004 | Kuehn | |
| 2004/0097788 A1 | 5/2004 | Mourles et al. | |
| 2004/0098112 A1 | 5/2004 | DiMatteo et al. | |
| 2004/0106976 A1 | 6/2004 | Bailey et al. | |
| 2004/0106990 A1 | 6/2004 | Spence et al. | |
| 2004/0111096 A1 | 6/2004 | Tu et al. | |
| 2004/0116951 A1 | 6/2004 | Rosengart | |
| 2004/0117004 A1 | 6/2004 | Osborne et al. | |
| 2004/0122468 A1 | 6/2004 | Yodfat et al. | |
| 2004/0122514 A1 | 6/2004 | Fogarty et al. | |
| 2004/0122516 A1 | 6/2004 | Fogarty | |
| 2004/0127979 A1 | 7/2004 | Wilson | |
| 2004/0138742 A1 | 7/2004 | Myers et al. | |
| 2004/0138743 A1 | 7/2004 | Myers et al. | |
| 2004/0153146 A1 | 8/2004 | Lashinski et al. | |
| 2004/0167573 A1 | 8/2004 | Williamson | |
| 2004/0167620 A1 | 8/2004 | Ortiz | |
| 2004/0186514 A1 | 9/2004 | Swain et al. | |
| 2004/0186563 A1 | 9/2004 | Lobbi | |
| 2004/0193261 A1 | 9/2004 | Berreklouw | |
| 2004/0210240 A1 | 10/2004 | Saint | |
| 2004/0210304 A1 | 10/2004 | Seguin et al. | |
| 2004/0210307 A1 | 10/2004 | Khairkhahan | |
| 2004/0215333 A1 | 10/2004 | Duran | |
| 2004/0215339 A1 | 10/2004 | Drasler et al. | |
| 2004/0220655 A1 | 11/2004 | Swanson et al. | |

(56) References Cited

U.S. PATENT DOCUMENTS

| | | |
|---|---|---|
| 2004/0225353 A1 | 11/2004 | McGuckin, Jr |
| 2004/0225354 A1 | 11/2004 | Allen |
| 2004/0236411 A1 | 11/2004 | Sarac et al. |
| 2004/0254636 A1 | 12/2004 | Flagle et al. |
| 2004/0260383 A1 | 12/2004 | Stelter et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0038495 A1 | 2/2005 | Greenan |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075713 A1* | 4/2005 | Biancucci ............... A61F 2/243 623/2.18 |
| 2005/0075717 A1 | 4/2005 | Nguyen |
| 2005/0075719 A1 | 4/2005 | Bergheim |
| 2005/0075720 A1 | 4/2005 | Nguyen et al. |
| 2005/0075724 A1 | 4/2005 | Svanidze |
| 2005/0075725 A1 | 4/2005 | Rowe |
| 2005/0075727 A1 | 4/2005 | Wheatley |
| 2005/0075728 A1* | 4/2005 | Nguyen ............... A61F 2/2418 623/1.26 |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug |
| 2005/0137695 A1 | 6/2005 | Salahieh |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0182483 A1 | 8/2005 | Osborne et al. |
| 2005/0185483 A1 | 8/2005 | Osborne et al. |
| 2005/0187616 A1 | 8/2005 | Realyvasquez |
| 2005/0192527 A1 | 9/2005 | Gharib et al. |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283231 A1 | 12/2005 | Haug et al. |
| 2005/0283962 A1 | 12/2005 | Boudjemline |
| 2005/0288764 A1 | 12/2005 | Snow et al. |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0020327 A1 | 1/2006 | Lashinski et al. |
| 2006/0025855 A1 | 2/2006 | Lashinski et al. |
| 2006/0025857 A1* | 2/2006 | Bergheim ............... A61L 27/50 623/2.18 |
| 2006/0047297 A1 | 3/2006 | Case |
| 2006/0047338 A1 | 3/2006 | Jenson et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0074484 A1 | 4/2006 | Huber |
| 2006/0074485 A1 | 4/2006 | Realyvasquez |
| 2006/0089711 A1 | 4/2006 | Dolan |
| 2006/0095119 A1 | 5/2006 | Bolduc |
| 2006/0100685 A1 | 5/2006 | Seguin et al. |
| 2006/0111771 A1 | 5/2006 | Ton et al. |
| 2006/0116757 A1 | 6/2006 | Lashinski et al. |
| 2006/0122686 A1 | 6/2006 | Gilad et al. |
| 2006/0122692 A1* | 6/2006 | Gilad .................... A61F 2/2418 623/1.35 |
| 2006/0135964 A1 | 6/2006 | Vesely |
| 2006/0142848 A1 | 6/2006 | Gabbay |
| 2006/0149360 A1 | 7/2006 | Schwammenthal et al. |
| 2006/0167474 A1 | 7/2006 | Bloom et al. |
| 2006/0173524 A1 | 8/2006 | Salahieh et al. |
| 2006/0178740 A1* | 8/2006 | Stacchino ............... A61F 2/848 623/2.18 |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0224227 A1 | 10/2006 | Chobotov |
| 2006/0235509 A1 | 10/2006 | Lafontaine |
| 2006/0241745 A1 | 10/2006 | Solem |
| 2006/0247570 A1 | 11/2006 | Pokorney |
| 2006/0247763 A1 | 11/2006 | Slater |
| 2006/0253191 A1* | 11/2006 | Salahieh ............... A61F 2/2439 623/2.11 |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1* | 11/2006 | Artof ...................... A61F 2/243 623/2.11 |
| 2006/0265056 A1 | 11/2006 | Nguyen et al. |
| 2006/0271097 A1 | 11/2006 | Ramzipoor et al. |
| 2006/0271149 A1 | 11/2006 | Berez et al. |
| 2006/0271166 A1 | 11/2006 | Thill et al. |
| 2006/0271175 A1 | 11/2006 | Woolfson et al. |
| 2006/0276813 A1 | 12/2006 | Greenberg |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2006/0287717 A1 | 12/2006 | Rowe et al. |
| 2007/0005129 A1 | 1/2007 | Damm et al. |
| 2007/0005131 A1 | 1/2007 | Taylor |
| 2007/0010876 A1 | 1/2007 | Salahieh et al. |
| 2007/0010878 A1 | 1/2007 | Raffiee et al. |
| 2007/0016281 A1 | 1/2007 | Melsheimer |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038291 A1* | 2/2007 | Case ....................... A61F 2/86 623/1.16 |
| 2007/0038295 A1 | 2/2007 | Case et al. |
| 2007/0043431 A1 | 2/2007 | Melsheimer |
| 2007/0043435 A1 | 2/2007 | Seguin et al. |

(56) References Cited

U.S. PATENT DOCUMENTS

| | | |
|---|---|---|
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100419 A1 | 5/2007 | Licata et al. |
| 2007/0100435 A1* | 5/2007 | Case .................. A61F 2/2418 623/901 |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0142907 A1 | 6/2007 | Moaddeb et al. |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0208550 A1* | 9/2007 | Cao .................. G06F 30/23 703/11 |
| 2007/0213813 A1 | 9/2007 | Von Segesser et al. |
| 2007/0225681 A1 | 9/2007 | House |
| 2007/0232898 A1 | 10/2007 | Huynh et al. |
| 2007/0233222 A1 | 10/2007 | Roeder et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239261 A1 | 10/2007 | Bose et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0255398 A1 | 11/2007 | Yang et al. |
| 2007/0260327 A1 | 11/2007 | Case et al. |
| 2007/0288000 A1 | 12/2007 | Bonan |
| 2007/0288087 A1* | 12/2007 | Fearnot .................. A61F 2/2418 623/2.18 |
| 2008/0004688 A1* | 1/2008 | Spenser .................. A61F 2/9524 623/2.14 |
| 2008/0004696 A1 | 1/2008 | Vesely |
| 2008/0009934 A1 | 1/2008 | Schneider et al. |
| 2008/0009940 A1 | 1/2008 | Cribier |
| 2008/0015671 A1 | 1/2008 | Bonhoeffer |
| 2008/0021546 A1* | 1/2008 | Patz .................. A61F 2/2433 623/2.11 |
| 2008/0021552 A1 | 1/2008 | Gabbay |
| 2008/0027529 A1 | 1/2008 | Hartley et al. |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1* | 3/2008 | Tuval .................. A61F 2/2469 623/2.1 |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082159 A1 | 4/2008 | Tseng et al. |
| 2008/0082165 A1 | 4/2008 | Wilson et al. |
| 2008/0082166 A1 | 4/2008 | Styrec et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1* | 6/2008 | Benichou .................. A61F 2/2418 623/1.26 |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0208327 A1* | 8/2008 | Rowe .................. A61F 2/2427 604/509 |
| 2008/0215143 A1 | 9/2008 | Seguin et al. |
| 2008/0215144 A1 | 9/2008 | Ryan et al. |
| 2008/0221666 A1 | 9/2008 | Licata et al. |
| 2008/0228254 A1 | 9/2008 | Ryan |
| 2008/0228263 A1 | 9/2008 | Ryan |
| 2008/0234797 A1 | 9/2008 | Stryc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1* | 10/2008 | Straubinger .................. A61F 2/2436 623/2.36 |
| 2008/0262592 A1 | 10/2008 | Jordan et al. |
| 2008/0262593 A1 | 10/2008 | Ryan et al. |
| 2008/0269878 A1 | 10/2008 | Iobbi |
| 2008/0275540 A1 | 11/2008 | Wen |
| 2008/0281403 A1 | 11/2008 | Kavteladze |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0062907 A1 | 3/2009 | Quijano et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171431 A1 | 7/2009 | Swanson et al. |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198315 A1 | 8/2009 | Boudjemline |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0259306 A1 | 10/2009 | Rowe |
| 2009/0270972 A1 | 10/2009 | Lane |
| 2009/0281619 A1 | 11/2009 | Le et al. |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0049306 A1 | 2/2010 | Bonhoeffer |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0100176 A1* | 4/2010 | Elizondo .................. A61F 2/2418 623/2.38 |
| 2010/0131054 A1 | 5/2010 | Tuval et al. |
| 2010/0137979 A1 | 6/2010 | Tuval et al. |

(56) References Cited

U.S. PATENT DOCUMENTS

| | | |
|---|---|---|
| 2010/0145435 A1 | 6/2010 | Voinov et al. |
| 2010/0145439 A1 | 6/2010 | Seguin et al. |
| 2010/0152840 A1 | 6/2010 | Seguin et al. |
| 2010/0174362 A1 | 7/2010 | Straubinger et al. |
| 2010/0198346 A1 | 8/2010 | Keogh et al. |
| 2010/0204781 A1 | 8/2010 | Alkhatib |
| 2010/0204785 A1* | 8/2010 | Alkhatib ............ A61F 2/2433 623/2.37 |
| 2010/0217382 A1* | 8/2010 | Chau ................ A61F 2/2418 623/2.12 |
| 2010/0234940 A1 | 9/2010 | Dolan |
| 2010/0249894 A1* | 9/2010 | Oba .................. A61F 2/2418 623/2.18 |
| 2010/0249923 A1 | 9/2010 | Alkhatib et al. |
| 2010/0256723 A1 | 10/2010 | Murray |
| 2010/0262157 A1 | 10/2010 | Silver et al. |
| 2010/0292785 A1 | 11/2010 | Sequin et al. |
| 2010/0305685 A1* | 12/2010 | Millwee ............ A61F 2/2418 623/1.26 |
| 2010/0331972 A1 | 12/2010 | Pintor et al. |
| 2011/0029066 A1 | 2/2011 | Gilad et al. |
| 2011/0098800 A1* | 4/2011 | Braido .............. A61F 2/2418 623/1.26 |
| 2011/0098802 A1* | 4/2011 | Braido .............. A61F 2/2466 623/2.11 |
| 2011/0125244 A1 | 5/2011 | Roeder et al. |
| 2011/0125258 A1* | 5/2011 | Centola ............ A61F 2/2418 623/2.38 |
| 2011/0137397 A1 | 6/2011 | Chau et al. |
| 2011/0166636 A1* | 7/2011 | Rowe ................ A61F 2/2427 623/1.26 |
| 2011/0208283 A1 | 8/2011 | Rust |
| 2011/0224780 A1 | 9/2011 | Tabor et al. |
| 2011/0257729 A1 | 10/2011 | Spenser et al. |
| 2011/0264191 A1* | 10/2011 | Rothstein ............ A61F 2/2436 623/1.11 |
| 2011/0295361 A1 | 12/2011 | Claiborne, III et al. |
| 2012/0078347 A1* | 3/2012 | Braido ................ A61F 2/915 623/1.26 |
| 2012/0078357 A1 | 3/2012 | Conklin |
| 2012/0089223 A1 | 4/2012 | Nguyen et al. |
| 2012/0101567 A1 | 4/2012 | Jansen |
| 2012/0172982 A1 | 7/2012 | Stacchino et al. |
| 2012/0296418 A1* | 11/2012 | Bonyuet ............ A61F 2/2415 623/2.18 |
| 2013/0096664 A1* | 4/2013 | Goetz ................ A61F 2/2412 623/1.26 |
| 2013/0253643 A1 | 9/2013 | Rolando et al. |
| 2014/0155997 A1* | 6/2014 | Braido .............. A61F 2/2433 623/2.37 |
| 2014/0257475 A1 | 9/2014 | Gross et al. |
| 2014/0343671 A1* | 11/2014 | Yohanan .......... A61F 2/2418 623/2.18 |
| 2015/0018944 A1* | 1/2015 | O'Connell ........ A61F 2/2427 623/2.42 |
| 2015/0112421 A1* | 4/2015 | Barnes .............. A61F 2/2412 623/2.11 |
| 2015/0127093 A1 | 5/2015 | Hosmer et al. |
| 2020/0000585 A1 | 1/2020 | Hariton et al. |
| 2021/0282923 A1* | 9/2021 | Armer .............. A61F 2/2418 |

FOREIGN PATENT DOCUMENTS

| | | |
|---|---|---|
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 814 | 4/2002 |
| DE | 100 49 815 | 4/2002 |
| EP | 0103546 | 3/1984 |
| EP | 0597967 | 12/1994 |
| EP | 0850607 | 7/1998 |
| EP | 1057459 | 6/2000 |
| EP | 1057460 | 6/2000 |
| EP | 1088529 | 4/2001 |
| EP | 1239795 | 9/2002 |
| EP | 1255510 | 11/2002 |
| EP | 0937439 | 9/2003 |
| EP | 0819013 | 6/2004 |
| EP | 1340473 | 6/2004 |
| EP | 1440673 | 7/2004 |
| FR | 2788217 | 12/1999 |
| FR | 2815844 | 5/2000 |
| GB | 2056023 | 3/1981 |
| GB | 2398245 | 3/2007 |
| GB | 2433700 | 12/2007 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/41789 | 11/2001 |
| WO | 02/22054 | 3/2002 |
| WO | 02/36048 | 5/2002 |
| WO | 02/47575 | 6/2002 |
| WO | 02/43620 | 7/2002 |
| WO | 03/003943 | 1/2003 |
| WO | 03/003949 | 1/2003 |
| WO | 02/49540 | 2/2003 |
| WO | 03/011195 | 2/2003 |
| WO | 03/030776 | 4/2003 |
| WO | 04/019811 | 3/2004 |
| WO | 04/019825 | 3/2004 |
| WO | 04/023980 | 3/2004 |
| WO | 04/041126 | 5/2004 |
| WO | 04/058106 | 8/2004 |
| WO | 04/089250 | 10/2004 |
| WO | 05/004753 | 1/2005 |
| WO | 05/027790 | 3/2005 |
| WO | 05/046528 | 5/2005 |
| WO | 05/062980 | 7/2005 |
| WO | 05/079151 | 9/2005 |
| WO | 07/022496 | 2/2007 |
| WO | 08/047354 | 4/2008 |
| WO | 08/079962 | 7/2008 |
| WO | 08/100599 | 8/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

(56) References Cited

OTHER PUBLICATIONS

Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
European Patent Office Communication in Application No. 09704087.7-2320, dated Nov. 30, 2012, 5 pages.
Expert report of Dr. Nigel Buller, dated Jan. 12, 2009, Edwards' United Kingdom action for invalidity, Claim No. HC 08CO0934 (83 pages).
Expert report of Dr. Nigel Buller, non-confidential annex—infringement, dated Jan. 12, 2009, Edwards' United Kingdom action for invalidity, Claim No. HC 08CO0934 (12 pages).
Expert report of Dr. Rodolfo Quijano, dated Jan. 9, 2009, *Edwards' LifeSciences* v. *Cook Biotech Incorporated*, United Kingdom action for invalidity, Claim No. HC 08CO0934 (18 pages).
First Expert report of Dr. Nigel Person Buller (30 pages), *Corevalve, Inc.* v. *Edwards Lifesciences Ag and Edwards Lifesciences PVT, Inc.*, High Court of Justice—Chancery Division Patents Court, United Kingdom, Case No. HC-07-C01243.
First Expert report of Prof. David Williams, dated Jan. 12, 2009, Edwards' United Kingdom action for invalidity, Claim No. HC 08CO0934 (41 pages).
Hanzel, et al., "Complications of percutaneous aortic valve replacement: experience with the Criber-Edwards™ percutaneous heart valve," EuroIntervention Supplements (2006), 1 (Supplement A) A3-A8.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Lutter, et al, "Percutaneous Aortic Valve Replacement: An Experimental Study. I. Studies on Implantation," the Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pasupati et al., "Transcatheter Aortic Valve Implantation Complicated by Acute Structural Valve Failure Requiring Immediate Valve in Valve Implantation," Heart, Lung and Circulation 2010; doi:10.1016/j.hlc.2010.05.006.
Pavcnik et al., "Aortic and venous valve for percutaneous insertion," Min. Invas. Ther. & Allied Techol. 2000, vol. 9, pp. 287-292.
Pelton et al., "Medical Uses of Nitinol," Materials Science Forum Vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Webb, et al., "Percutaneous Aortic Valve Implantation Retrograde from the Femoral Artery," Circulation (2006), 113;842-850.
Extended European Search Report, EP application No. 20186125.9, dated Oct. 15, 2020.
Communication Pursuant to Article 94(3) EPC (European Office action), EP application No. 20186125.9, dated Aug. 3, 2021.

* cited by examiner

STENTS FOR PROSTHETIC HEART VALVES

CROSS-REFERENCE TO RELATED APPLICATION

The present application is a continuation of and claims priority to U.S. patent application Ser. No. 16/932,779, filed Jul. 19, 2020, which is a continuation of and claims priority to U.S. patent application Ser. No. 15/099,075, filed Apr. 14, 2016, now U.S. Pat. No. 10,758,343, which is a continuation of and claims priority to U.S. patent application Ser. No. 14/087,990, filed Nov. 22, 2013, now U.S. Pat. No. 9,333,100, which is a continuation of and claims priority to U.S. patent application Ser. No. 12/358,980, filed Jan. 23, 2009, now U.S. Pat. No. 8,628,566, which claims priority to U.S. Provisional Application No. 61/062,207, filed Jan. 24, 2008, the entire contents of which are incorporated herein by reference in their entirety.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion, of a catheter until it is as close to the diameter of the catheter as possible.

Other percutaneously-delivered prosthetic heart valves have been suggested having a generally similar configuration, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different designs of cardiac valves that can be implanted in a minimally invasive and percutaneous manner.

SUMMARY

The replacement heart valves of the invention each include a stent to which a valve structure is attached. The stents of the invention include a wide variety of structures and features that can be used alone or in combination with features of other stents of the invention. In particular, these stents provide a number of different docking and/or anchoring structures that are conducive to percutaneous delivery thereof. Many of the structures are thus compressible to a relatively small diameter for percutaneous delivery to the heart of the patient, and then are expandable either via removal of external compressive forces (e.g., self-expanding stents), or through application of an outward radial force (e.g., balloon expandable stents). The devices delivered by the delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. In addition, delivery methods of the invention can include features that allow the stents to be retrieved for removal or relocation thereof after they have been deployed or partially deployed from the stent delivery systems. The methods may include implantation of the stent structures using either an antegrade or retrograde approach. Further, in many of the delivery approaches of the invention, the stent structure is rotatable in vivo to allow the stent structure to be positioned in a desired orientation.

One embodiment of a stent of the invention comprises a tubular wire structure including multiple longitudinal wires that extend generally parallel to the longitudinal axis of the stent. The wires are spaced from each other around the periphery of the stent. The stent further includes tissue attachment features, such as commissure attachment posts. In one embodiment, the stent includes three commissure attachment posts, where each of the posts is used as a connection location for one of the commissures of a tri-leaflet valve that will be attached thereto. Alternatively, more or less than three posts can be provided for a valve having more or less than three leaflets, respectively. The stent further includes multiple V-shaped wire structures between a pair of wires and/or between a wire and an adjacent attachment post. In one embodiment, the stent includes three V-shaped wires that are longitudinally spaced from each other along the height of the stent between each adjacent pair of wires or between a wire and an adjacent post. There may alternatively be more or less than three V-shaped wires spaced longitudinally from each other.

A first end of each V-shaped wire extends from a first end of an attachment post or wire, and a second end of wire extends from the first end of an adjacent wire or attachment post. In this way, a peak of each V-shaped wire will be positioned generally in the center of the space between adjacent longitudinal wires, and will be directed toward a second or inlet end of the stent. All or some of the wires can be flared at least slightly outward relative to the outer tubular shape of the stent, thereby creating integrated flange structures that can be used to capture the native leaflets when the stent is implanted in a patient. Each wire is spaced longitudinally from a corresponding wire, and each wire is spaced longitudinally from a corresponding wire.

BRIEF DESCRIPTION OF THE DRAWINGS

The present invention will be further explained with reference to the appended Figures, wherein like structure is referred to by like numerals throughout the several views, and wherein:

FIG. 1.9 is a perspective view of the padded slot bar mechanism, tissue, and portion of a stent illustrated in FIG. 18;

DETAILED DESCRIPTION

Figure 1:
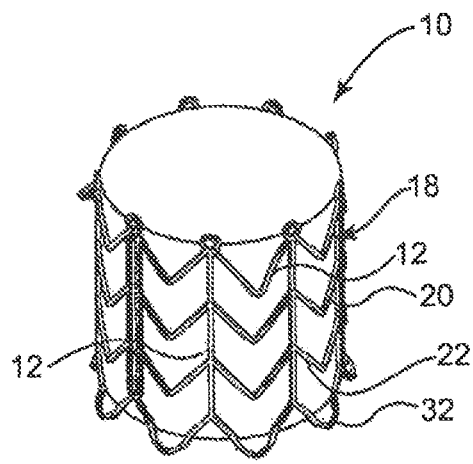
FIG. 1 is a perspective view of an embodiment of a stent in accordance with the invention.
Figure 2:
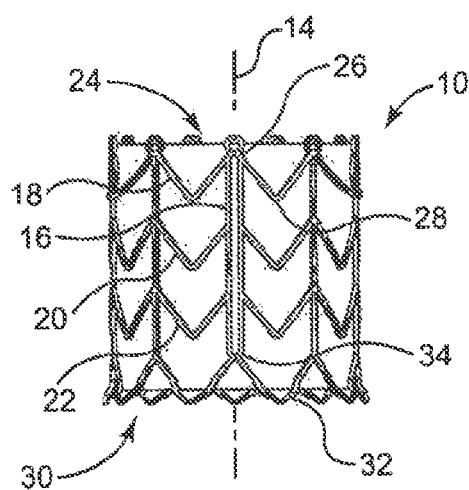
FIG. 2 is a front view of the stent of FIG. 1.

As referred to herein, the prosthetic heart valves used in accordance with the various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

Although each of the valves used with the delivery devices and methods described herein would typically include leaflets attached within an interior area of a stent, the leaflets are not shown in many of the illustrated embodiments for clarity purposes. In general, the stents described herein include a support structure comprising a number of strut or wire portions arranged relative to each other to provide a desired compressibility, strength, and leaflet attachment zone(s) to the heart valve. Other details on particular configurations of the stents of the invention are also described below; however, in general terms, stents of the invention are generally tubular support structures, and leaflets will be secured within the inner portion of the support structure to provide a valved stent. The leaflets can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the stent. In another alternative, the stent and leaflets can be fabricated at the same time, such as may be accomplished using high strength nano-manufactured NiTi films of the type produced at Advanced Bio Prosthetic Surfaces Ltd. (ABPS) of San Antonio, Tex., for example. The support structures are generally configured to accommodate three leaflets; however, the replacement prosthetic heart valves of the invention can be configured to incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets utilize certain features of known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:4.19-29; Block P C, "Clinical and Hemodynamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000:102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning the stents of the invention with native anatomical structures, they should be aligned so as to not block the coronary arteries, and native mitral or tricuspid valves should be aligned relative to the anterior leaflet and/or the trigones/commissures.

Some embodiments of the support structures of the stents described herein can be a series of wires or wire segments arranged so that they are capable of transitioning from a collapsed state to an expanded state. In some embodiments, a number of individual wires comprising the support structure can be formed of a metal or other material. These wires are arranged in such a way that a support structure allows for folding or compressing to a contracted state in which its internal diameter is greatly reduced from its internal diameter when it is in an expanded state. In its collapsed state, such a support structure with attached valves or leaflets can be mounted over a delivery device, such as a balloon catheter, for example. The support structure is configured so that it can be changed to its expanded state when desired, such as by the expansion of a balloon catheter. The delivery systems used for such a stent should be provided with degrees of rotational and axial orientation capabilities in order to properly position the stent at its desired location within the patient.

The wires of the support structure of the stents in other embodiments can alternatively be formed from a shape memory material such as a nickel titanium alloy (e.g., Nitinol). With this material, the support structure is self-expandable from a contracted state to an expanded state, such as by the application of heat, energy, and the like, or by the removal of external forces (e.g., compressive forces). This support structure can also be repeatedly compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand.

Referring now to the Figures, wherein the components are labeled with like numerals throughout the several Figures, and initially to FIGS. 1-4, an exemplary embodiment of a stent 10 is illustrated. Stent 10 may be referred to as a sub-coronary stent for use in replacement of the aortic valve in that it is preferably relatively short to enable stent placement below the coronaries. Stent 10 may be made of a self-expanding material, such as Nitinol, for example. In one embodiment, the stent 10 is generally tubular in shape and can be approximately 25 mm long, for example, although it can be longer or shorter than 25 mm, depending on the anatomy of the patient, the preferences of the surgeon, and other factors. The stent 10 includes multiple longitudinal or vertical wires 12 that extend generally parallel to a longitudinal axis 14 of the stent. The wires 12 are spaced from each other around the periphery of the generally tubular shape of the stent 10. Stent 10 further includes features to which tissue can be attached to make the stent into a valve, such as commissure attachment posts 16 that can be approximately 18 mm long, for example. The commissure attachment posts 16 each include two longitudinal wires that are spaced closer to each other than the spacing of the wires 12 from each other.

In this embodiment, stent 10 includes three commissure attachment posts 16, where each of the posts 16 is used as a connection location for one of the commissures of a tri-leaflet valve that will be attached thereto. Alternatively, more or less than three posts 16 can be provided for a valve having more or less than three leaflets, respectively. In addition to providing the structure for attachment of commissures, the posts 16 also provide additional stability to the stent 10. The wires 12 and posts 16 are preferably spaced at generally the same distance from each other around the periphery of the stent 10, although it is contemplated that some of the wires 12 and/or posts 16 can be spaced at different distances from each other around the periphery of the stent 10. Further, the specific illustrated embodiment of stent 10 includes two wires 12 positioned between two commissure attachment posts 16, although an alternate embodiment may include more or less wires 12 between adjacent commissure posts 16. However, the specific embodiment of stent 10 illustrated in FIGS. 1-4 comprises nine longitudinal structures around its periphery, including six longitudinal wires 12 and three commissure attachment posts 16.

Stent 10 further includes multiple V-shaped wire structures between a pair of wires 12 and/or between a wire 12 and an adjacent attachment post 16. As shown, the stent 10 includes three wires 18, 20, 22 that are longitudinally spaced from each other along the height of the stent 10 between each adjacent pair of wires 12 or between a wire 12 and an adjacent post 16. The size and shape of the wires 18, 20, 22 determines the spacing between adjacent longitudinal structures of the stent 10, which is generally uniform around the periphery of the stent, as discussed above. Although the stent 10 includes three of these V-shaped wires 18, 20, 22 that are spaced longitudinally from each other between adjacent vertical wire structures, there may be more or less than three V-shaped wires spaced longitudinally from each other.

Wires 18 are positioned at a first or outlet end 24 of the stent 10. A first end of each wire 18 extends from a first end 26 of an attachment post 16 or wire 12, and a second end of wire 18 extends from the first end 26 of an adjacent wire 12 or attachment post 16. In this way, a peak 28 of each wire 18 will be positioned generally in the center of the space between adjacent longitudinal wires, and will be directed toward a second or inlet end 30 of the stent 10. All or some of the wires 18 can be flared at least slightly outward relative to the outer tubular shape of the stent 10, thereby creating integrated flange structures that can be used to capture the native leaflets when the stent is implanted in a patient. Each wire 20 is spaced longitudinally from a corresponding wire 18, and each wire 22 is spaced longitudinally from a corresponding wire 20.

Additional wire structures 32 are positioned at the second end 30 of the stent 10 to correspond with each set of wires 18, 20, 22. In particular, each wire structure 32 is generally V-shaped, where the peak of each of the "V" structures is oriented in generally the same direction as the peaks of the wires 18, 20, 22. A first end of each wire structure 32 extends from a second end 34 of an attachment post 16 or wire 12, and a second end of wire structure 32 extends from the second end 34 of an adjacent wire 12 or attachment post 16. All or some of the wire structures 32 are flared at least slightly outward relative to the outer tubular shape of the stent 10. The amount and angle at which the wire structures extend relative to the tubular outer shape of the stent can be selected for capturing native patient anatomical features. In addition, this flare of the wire structures 32 can help to prevent or minimize leakage between the implant and the native annulus and/or to provide a physical and/or visual docking feature to secure the stent 10 against a wall of an opening in the heart to prevent migration of the stent, for example.

The stent 10 has a relatively high-density strut pattern to contain leaflets within the inner stent area during crimping of the stent. That is, while the exact number of longitudinal wires and V-shaped wires can vary somewhat from that illustrated in the Figures, it is preferable that the number of wires provided is sufficient to keep the leaflet material from becoming compressed and potentially damaged between the stent struts during the crimping process or from protruding beyond the periphery of the stent when it is in a crimped condition.

Figure 4:
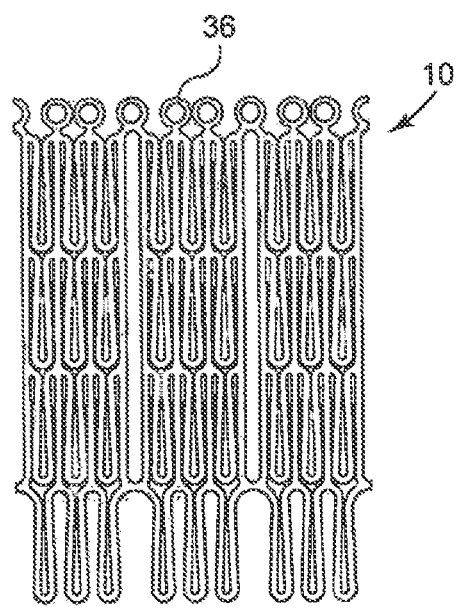
FIG. 4 is a top view of a cutting pattern for the stent of FIG. 1.
Figure 3:
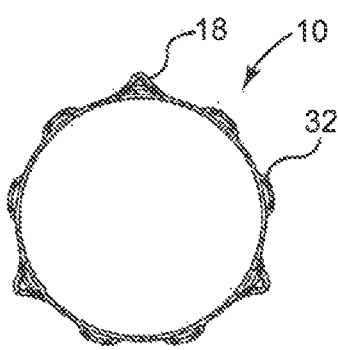
FIG. 3 is a top view of the stent of FIG. 1.
Figure 5:
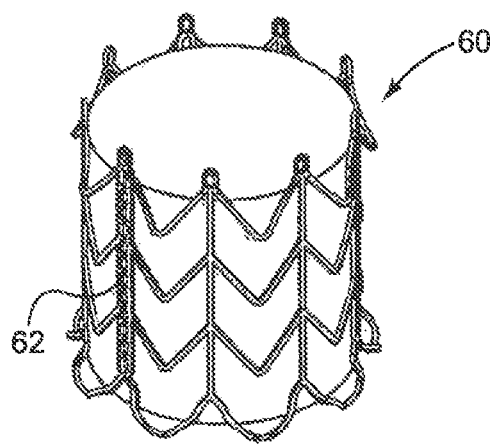
FIG. 5 is a perspective view of an embodiment of a stent in accordance with the invention.
Figure 6:
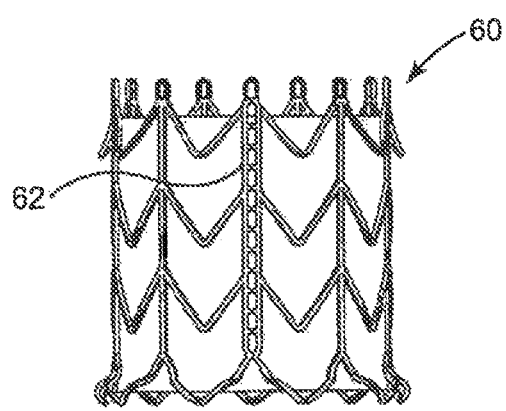
FIG. 6 is a front view of the stent of FIG. 5.
Figure 8:
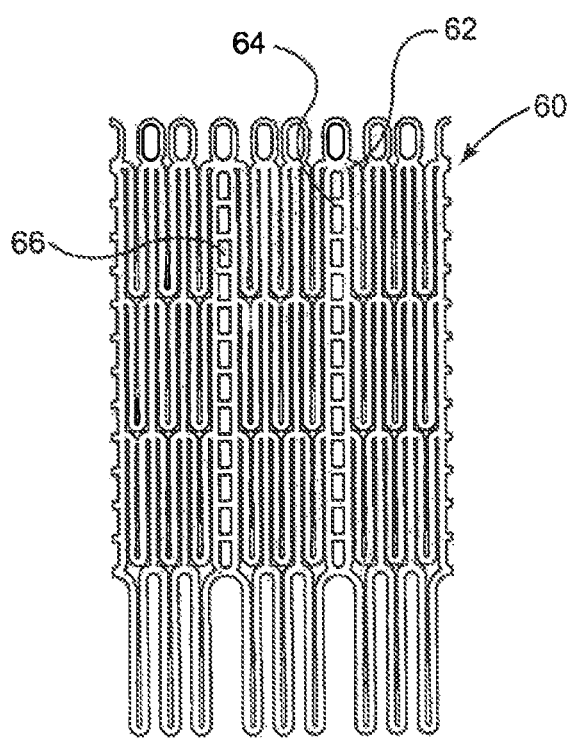
FIG. 8 is a top view a cutting pattern for the stent of FIG. 5.
Figure 7:
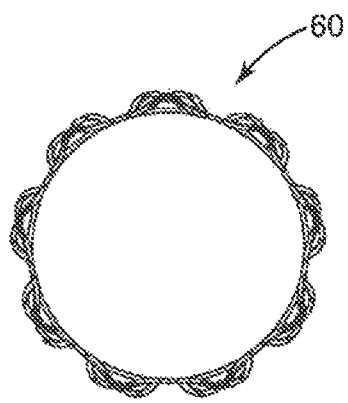
FIG. 7 is a top view of the stent of FIG. 5.

The first end 26 of all or some of the wires 12 and posts 16 can further include a loop or eyelet 36 that can be used for attachment to a delivery system and/or tissue valve, for example. The eyelets 36 can be in the same general plane as the outer tubular shape of the stent 10, or they can be directed at least slightly inward toward the central area of the stent or at least slightly outward relative to the outer tubular surface of the stent. The single-sided eyelet attachment end can be used in a resheathable delivery system for both antegrade and retrograde procedures, for example. Attachment end crown reducers can optionally be added to the stent to reduce the attachment crown number, although the stent would be lengthened at least slightly by such a modification, FIG. 4 illustrates an exemplary laser cutting pattern that can be used to form the stent 10 out of a tube or single sheet of material. The stent 10 can alternatively be made from multiple components that are attached to each other and formed into a tubular shape. However, if the stent will be cut from a tube or single sheet of material as shown, the various structures will be designed so that they do not interfere with each other in the pattern.

Figure 26:
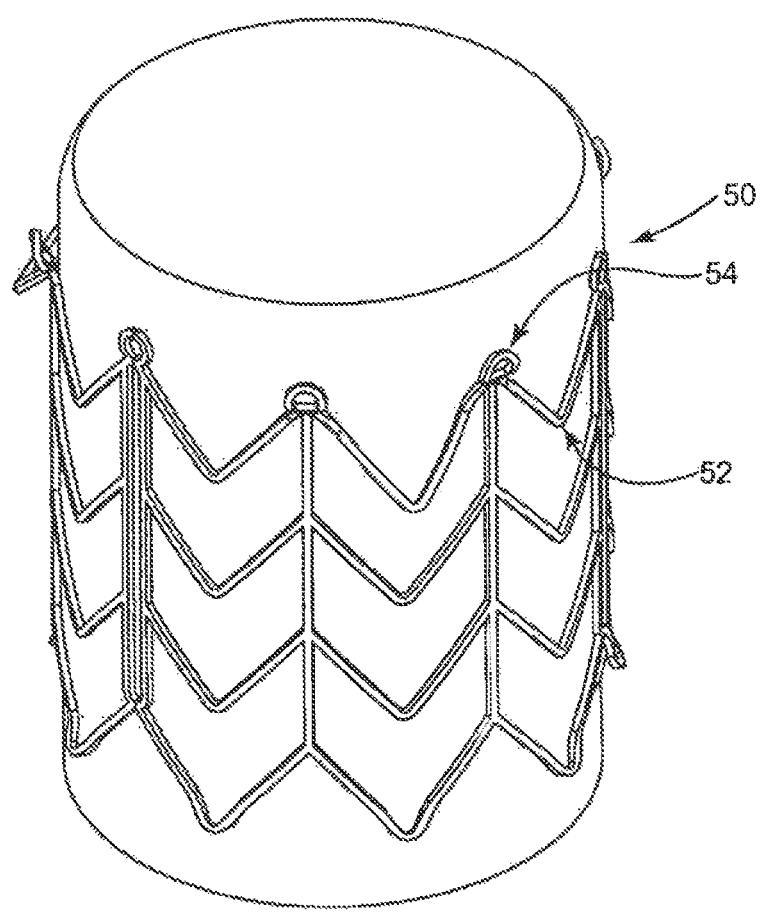
FIG. 26 is a perspective view of another stent embodiment of the invention.

FIG. 26 illustrates another exemplary embodiment of a stent 50 positioned for clarity on a mandrel, which also may be referred to as a sub-coronary stent in that it is preferably relatively short (e.g., 25 mm long) to enable stent placement below the coronary arteries in the aorta. This stent includes a number of the same features as the stent of FIGS. 1-4, although this stent 50 does not include the integrated petals shown and described above relative to stent 10. Rather, the V-shaped structures 52 at the outlet end of the stent 50 are generally in the same plane as the tubular outer shape of the stent 50 (i.e., the structures 52 are not flared outwardly). The stent 50 also includes eyelets 54 at the outlet end of the stent, which can be in the same general plane as the outer tubular shape of the stent 50, or they can be directed at least slightly inward or at least slightly outward relative to the outer tubular shape of the stent 50.

FIGS. 5-8 illustrate another exemplary embodiment of a stent 60, which is similar in structure to the stent 10 described above, including a wire structure with multiple commissure attachment posts 62. These posts 62 include two vertical struts that are spaced at least slightly from each other. These posts 62 further include multiple horizontal members 64 that are spaced from each other along the length or height of each post 62. The spaces or openings 66 that are created between the horizontal members 64 provide locations through which suture material, needles, and/or other fastening materials can be inserted for attachment of leaflet or valve material to the stent at the commissure posts. In addition, the horizontal members 64 can be used as defined anchoring points for the fastening materials. For example, a suture material can be inserted through a first opening 66 and then through another opening 66 in a predetermined pattern to stitch valve material to the commissure attachment posts 62. The horizontal members 64 can further be used as anchoring structures that keep sutures or other attachment mechanisms from moving vertically past a certain position along the attachment posts 62.

Figure 9:
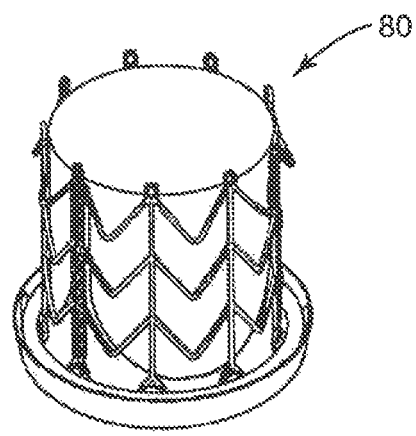
FIG. 9 is a perspective view of an embodiment of a stent in accordance with the invention.
Figure 10:
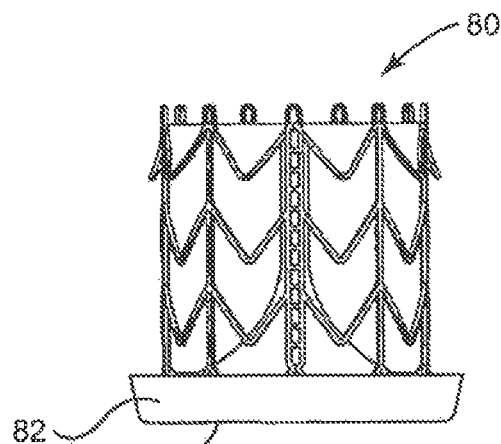
FIG. 10 is a front view of the stent of FIG. 9.
Figure 11:
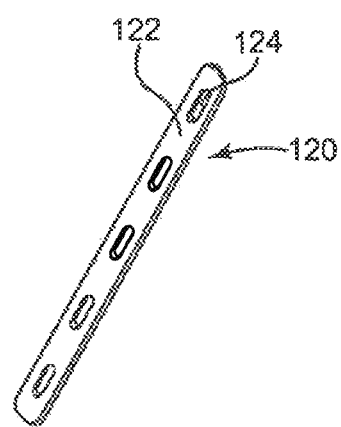
FIG. 11 is a perspective view of a "ladder" mechanism used for attachment of tissue to a stent.

Another embodiment of a sterit 80 is illustrated in FIGS. 9 and 10, which has a similar structure to stent structures described above relative to tubular stent constructions. Stent 80 further includes a sealing skirt 82 at its inlet end 84. The sealing skirt 82 can provide for improved sealing between the stent 80 and the anatomy in which the stent 80 is placed, such as the annulus of a valve, for example. The sealing skirt 82 can be configured to unfurl away from the inlet end 84 of the valve and into the delivery system that was used to deliver the stent 80, if desired. In this way, the material used to make the sealing skirt 82 does not increase the overall size of the stent 80 when it is crimped or compressed. The sealing skirt 82 can further be provided with radiopaque, echogenic properties or other visually detectable properties so that an operator can assess the proper positioning of the stent 80 in the patient's anatomy prior to releasing it from the delivery system.

A number of systems, components, and devices are described below for attachment of valve material (e.g., tissue leaflets) within the interior area of a stent structure. It is understood that the systems that are shown and described herein for this purpose can be used with stent configurations described above and/or other stent constructions.

In one exemplary embodiment, a tubular stent structure includes at least one commissure post, along with a first leaflet and a second leaflet. Leaflets are attached or sewn to the post using suture material. In this embodiment, a tissue "cushion" is provided on both sides of the commissure attachment post to help absorb and distribute stress away from the stitch points and to minimize tissue abrasion that can be caused without such protection. In this configuration, the leaflets 104, 106 can flex along the tissue and the leaflet/tissue seam line and the tissue cushion distributes stress from flexing during opening and closing of leaflets away from the suture points where leaflets are attached into the attachment post.

Another configuration and device that can be used in the attachment of valve material to a stent structure is shown and described relative to FIGS. 11-14. In particular, a relatively rigid "ladder" member 120 is provided to support the leaflet commissure area and transfer the line or point about which the leaflets 140 flex or bend to a location that is spaced from the suture line. In this way, the stresses can be more evenly distributed and durability of the valve improved. Ladder member 120 includes a relatively flat elongated plate 122 having multiple holes or openings 124 along its length. In order to minimize or prevent damage to the tissue of the valve, the corners and edges of the ladder member 120 are preferably rounded or smoothed. The holes 124 are preferably spaced from each other by a distance that corresponds with a desired stitching pattern that will be used to both secure the member 120 to the stent structure and attach the leaflets. It is further contemplated that the ladder member 120 is configured to match specific commissure features of the stent.

Figure 12:
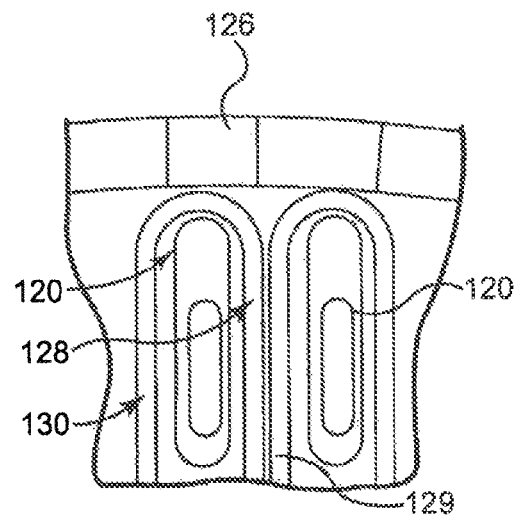
FIG. 12 is a top view of two ladder mechanisms of FIG. 11 positioned relative to leaflets and a stent.
Figure 13:
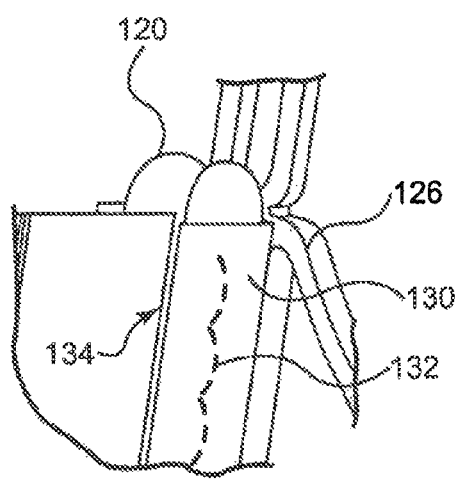
FIG. 13 is a perspective view of the ladder mechanisms, tissue, and portion of a stent illustrated in FIG. 12.

FIGS. 12 and 13 illustrate two ladder members 120 positioned relative to a portion of a stent 126 and portions of two leaflets. In particular, portions 128, 129 of adjacent leaflet commissures are secured in the space between two ladder members 120. The ladder members 120 are spaced from each other by a distance that allows the components to be securely fastened to each other, but that accommodates the thickness of the leaflets that are positioned between them. Additional material from the leaflets extends around the ends of the ladder members 120 between the edge of the ladder members 120 and the stent 126, then along the outwardly facing sides of the ladder members 120, such as is indicated by the reference number 130. This additional material provides for improved security in tissue attachment and also provides additional attachment locations.

Figure 15:
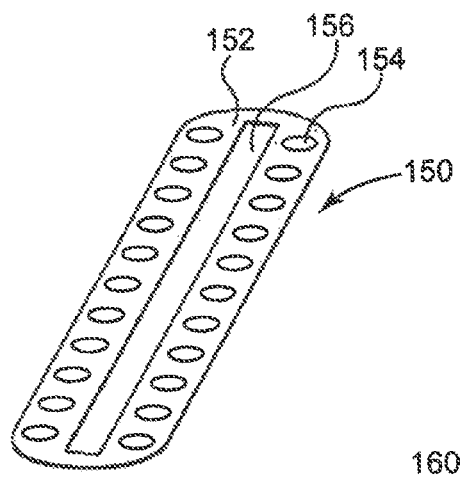
FIG. 15 is a perspective view of a "slot bar" mechanism used for attachment of tissue to a stent.

Sutures 132 can be inserted through the tissue material to secure it to the ladder members 120, where one exemplary stitching pattern is illustrated in FIG. 15. An appropriate number of stitches should be made through the tissue material and ladder member 120 to securely attach the ladder members 120 to the leaflets. The same or a different suture material can be used to attach or position adjacent ladder members 120 relative to each other. Additional sutures or an extension of the sewing pattern can also be used to connect the ladder members 120 to the stent 126. The suture pattern can follow the holes in the ladder member 120 such that the ladder member 120 provides a template for sewing the leaflet tissue to the ladder members 120, or an alternate stitching pattern can be used. The leaflets can then flex against a long vertical edge 134 of each of the ladder members 120, thereby transferring the stress away from the attachment suture line.

Figure 14:
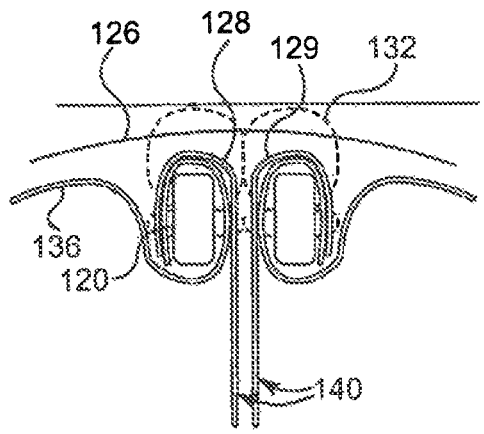
FIG. 14 is a top schematic view of the stent arrangement of FIGS. 12 and 13.

FIG. 14 illustrates another tissue attachment arrangement that includes the use of two ladder members 120, as described above, along with additional protective layers 136. Each protective layer 136 can provide supplemental padding between a ladder and the adjacent leaflet material, and can also provide additional strength at the attachment sites. The protective layers 136 can be made of a material such as cloth, tissue, polymeric sheets, or the like. As shown, one protective layer 136 is used for each of the ladder members 120, with the protective layer 136 being positioned between each ladder member 120 and its corresponding leaflet 128, 129. Each protective layer 136 can wrap around at least a portion of the periphery of its corresponding ladder member 120, and in one embodiment will wrap around almost the entire periphery of the ladder members 120, as shown. Further, each protective layer 136 can extend along the entire length or height of its corresponding ladder 120, or it may extend along only a portion of the length of the ladder member 120. An exemplary pattern of stitching the components to each other and to the stent 126 is illustrated with the sutures 132 (shown as broken lines), although a different stitching pattern can instead be used.

Figure 16:
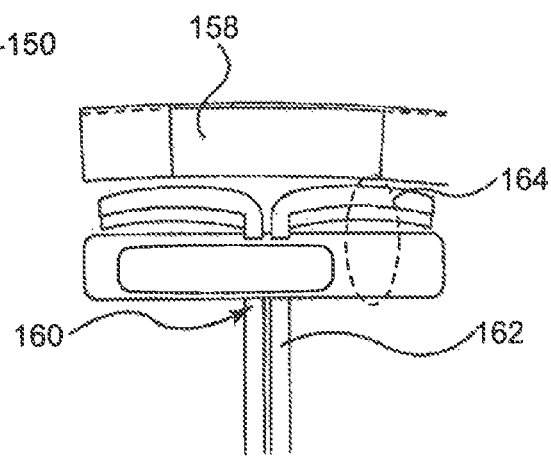
FIG. 16 is a top view of a slot bar mechanism of FIG. 15 positioned relative to leaflets and a stent.
Figure 17:
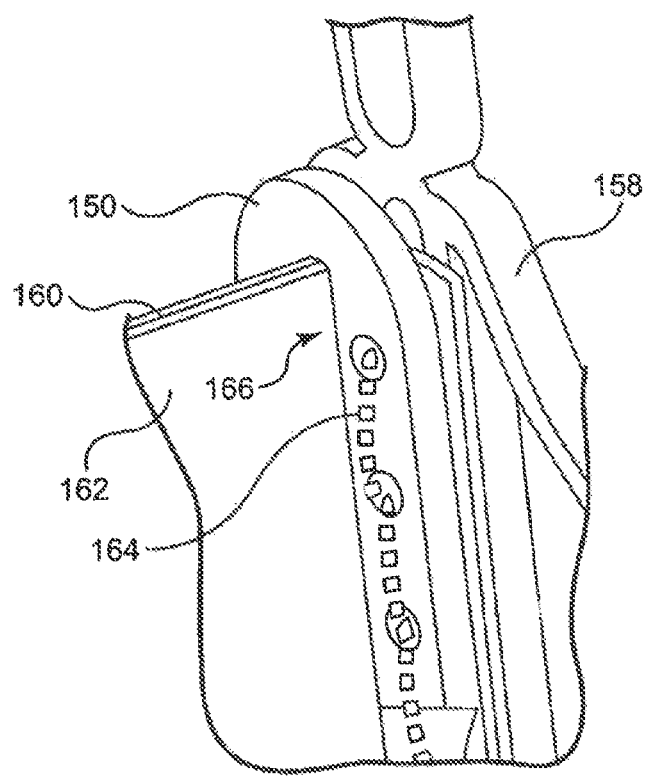
FIG. 17 is perspective view of the slot bar mechanism, tissue, and portion of a stent illustrated in FIG. 16.

Another configuration and device that can be used in the attachment of valve material to a stent structure is shown and described relative to FIGS. 15-17. In particular, a relatively rigid "slot bar" member 150 is provided to support the leaflet commissure area and transfer the line or point about which the leaflets flex or bend to a location that is spaced from the suture line. In this way, the stresses can be more evenly distributed. Slot bar member 150 includes a relatively flat elongated plate 152 having a longitudinal slot 156 extending along a portion of its length, and multiple holes or openings 154 along the length of the member 150 on both sides of the slot 156. Alternatively, one or both ends could be open and/or two separate portions can make up the slot bar member. In order to minimize or prevent damage to the tissue of the valve, the corners and edges of the slot bar member 150 are preferably rounded or smoothed. The holes 154 are preferably spaced from each other by a distance that corresponds with a desired stitching pattern that will be used to both secure the member 150 to the stent structure and the tissue to the slot bar. It is further contemplated that the slot bar member 150 is configured to match specific commissure features of the stent to which it will be attached. In addition, the width of the slot 156 is preferably selected based on the thickness of the leaflets that will be inserted through the slot 156. Thus, the slot 156 should be wide enough to accommodate two thicknesses of leaflet material; however, the slot 156 may be designed for more layers of material or for an optimized compression fit, if desired. In order to provide secure positioning of the tissue layers within the slot 156 and to minimize the potential for the tissue to be pulled from the slot 156, the slot should not be substantially wider than the thickness of the materials that will be positioned within it.

FIGS. 16-17 illustrate slot bar member 150 positioned relative to a portion of a stent 158 and portions of two leaflets 160, 162. In particular, the end portions of adjacent leaflet commissures 160, 162 are pulled through the slot 156 by a sufficient distance that the free edge of each of the leaflets extends at least slightly past the holes 154 on the flat side of the plate 152. This end portion of the leaflets 160, 162 will thereby be positioned between the slot bar member 150 and the stent to which they will be attached. In this way, the leaflets 160, 162 can be securely fastened to the slot bar member 150 and the stent 158. Sutures 164 can then be inserted through the tissue material to secure it to the slot bar member 150, where one exemplary stitching pattern is illustrated in FIGS. 16 and 17. The stitching pattern can follow the holes 154 in the slot bar member 150 such that the slot bar member 150 provides the template for sewing the leaflet tissue to the slot bar member 150, or an alternate stitching pattern can be used. The sutures 164 can thereby connect the slot bar member 150 to the leaflets 160, 162. Additional sutures or the same sutures can also be used to connect the slot bar member 150 to the stent 158. The leaflets 160, 162 can then flex over a long vertical edge 166 on each side of the slot bar member 150 during valve leaflet opening and closing, thereby transferring the stress away from the attachment suture line and increasing the durability of the valve.

Figure 18:
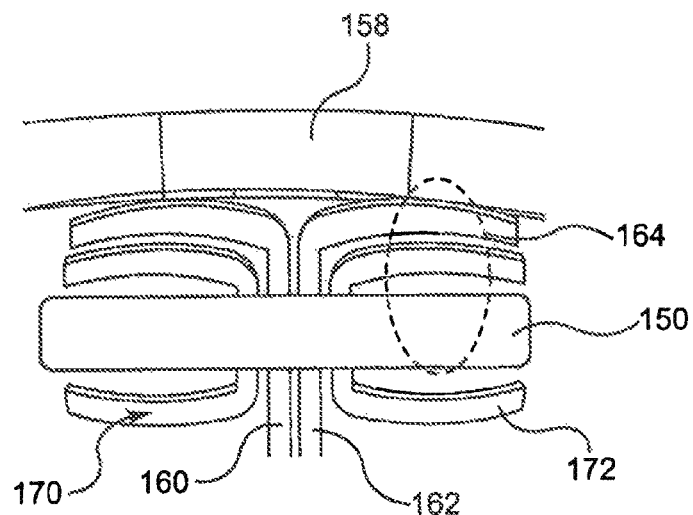
FIG. 18 is a top view of a "padded slot bar" mechanism positioned relative to leaflets and a stent.
Figure 19:
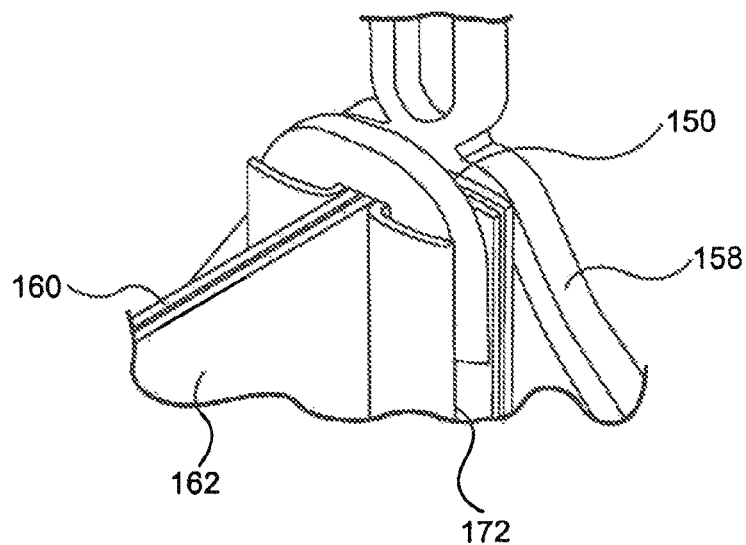

FIGS. 18 and 19 illustrate another tissue attachment arrangement that includes the use of a slot bar member 150 of the type described above, along with additional protective members 170, 172. Protective members 170, 172 are positioned on opposite sides of the slot 156 of the slot bar member 150 so that each of the members 170, 172 can protect one of the leaflets 160, 162. Each protective member 170, 172 can provide additional padding or cushioning between one of the leaflets 160, 162 and the slot bar member 150 during opening and closing of the leaflets. The protective members 170, 172 can be made of a material such as cloth, tissue, polymeric sheets, or the like. Further, each protective member 170, 172 can extend along the entire length of its corresponding slot bar member 150, or it may extend along only a portion of the length of the slot bar member 150. An exemplary pattern of stitching the components to each other and to the stent 158 is illustrated with the schematic representation of a suture 164, although a different stitching pattern can instead be used. The suture material can be used to attach the excess tissue material to only the slot bar member 150, if desired. Alternatively, the protective members on the leaflet side of the slot bar member could be extended circumferentially beyond the slot bar member and attached to the stent (not shown). In this way, the leaflet would be prevented from contacting the suture material during opening of the valve reducing the potential for leaflet abrasion and tearing. In order to accommodate the thickness of the extra layers provided by the protective members 170, 172, the slot 156 should have an appropriate width.

Figure 20:
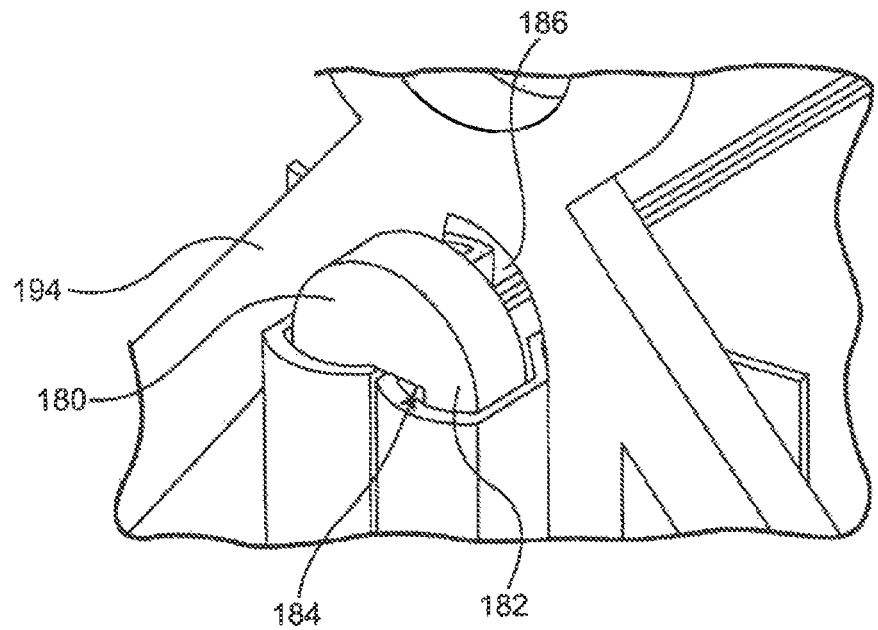
FIG. 20 is a perspective view of a "buckle" mechanism positioned relative to leaflets and a stent.
Figure 21:
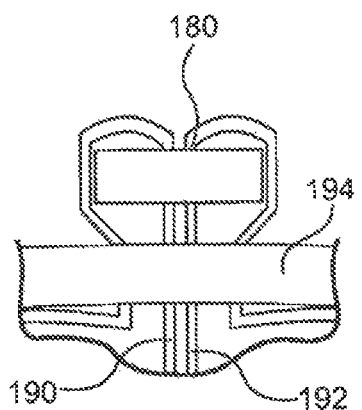
FIG. 21 is a top view of the portion of a stent, leaflets, and buckle mechanism illustrated in FIG. 20.
Figure 22:
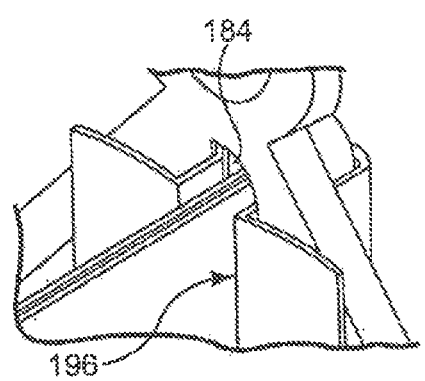
FIG. 22 is another perspective view of the portion of a stent illustrated in FIG. 20.

Another configuration and device that can be used in the attachment of valve material to a stent structure is shown and described relative to FIGS. 20-22. In particular, a relatively rigid "buckle" member 180 is provided to support the leaflet commissure area and transfer the line or point about which the leaflets flex or bend to a location that is spaced away from the suture line. In this way, the stresses can be more evenly distributed increasing the durability of the valve. Buckle member 180 includes a relatively flat elongated plate 182 having a longitudinal slot 184 extending along a portion of its length. The slot could alternatively be open at either one or both ends of the plate. In order to minimize or prevent damage to the tissue of the valve, the corners and edges of the buckle member 180 are preferably rounded or smoothed. The width of the slot 184 is preferably selected based on the thickness of the layers of material that will be inserted through the slot 184. Thus, the slot 184 should be wide enough to accommodate the two thicknesses of leaflet material that will extend through it, as described below; however, the slot 184 may be designed for more layers of material or for an optimized compression fit, if desired. In order to provide secure positioning of the tissue layers within the slot 184 and to minimize the potential for the tissue to be pulled from the slot 184, the slot should not be substantially wider than the width of the material that will be positioned within it.

As shown in the Figures, the buckle member 180 is positioned on the opposite side of a stent 194 than the other embodiments discussed above (i.e., on the outer side of the stent structure rather than on the inner side of the stent structure). In this embodiment, the stent 194 has a vertical slot 186 in its commissure post that generally corresponds to the slot 184 in the buckle member 180. The end portions of two leaflets 190, 192 are pulled through the slot 186 in the stent commissure post, then through the slot 184 in the buckle member 180. The ends of the leaflets are then wrapped around the back side of the buckle member 180 and pulled back through the slot 186 in the commissure post in the opposite direction than the first insertion of the leaflets through this slot 186. The leaflets 190, 192 should continue to be pulled through the slot 186 by a sufficient distance that the free edge of each of the leaflets 190, 192 extends at least slightly past the structure of the stent in the internal area of the stent. With this arrangement, the leaflets 190, 192 will flex generally along a vertical line 196, which is the tissue that covers a vertical edge of the stent. In this embodiment, no sutures are required for attachment of the leaflets 190, 192 to the stent and/or the buckle member 180. Rather, the force on the commissure caused by the closing of the leaflets 190, 192 will cause the buckle member 180 to be pressed toward the stent, thereby compressing and locking the excess tissue material between the buckle member and the stent. This secures the commissure and prevents the tissue material of the leaflets from pulling out of the assembly.

Figure 23:
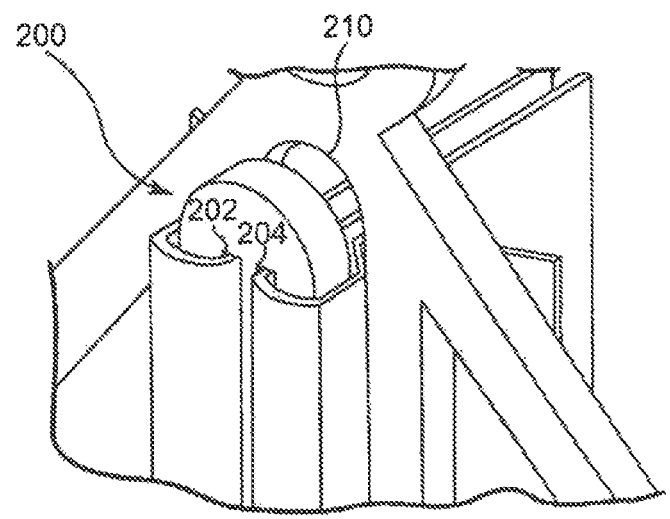
FIG. 23 is a perspective view of a "padded buckle" mechanism positioned relative to leaflets and a stent.
Figures 24, 25:
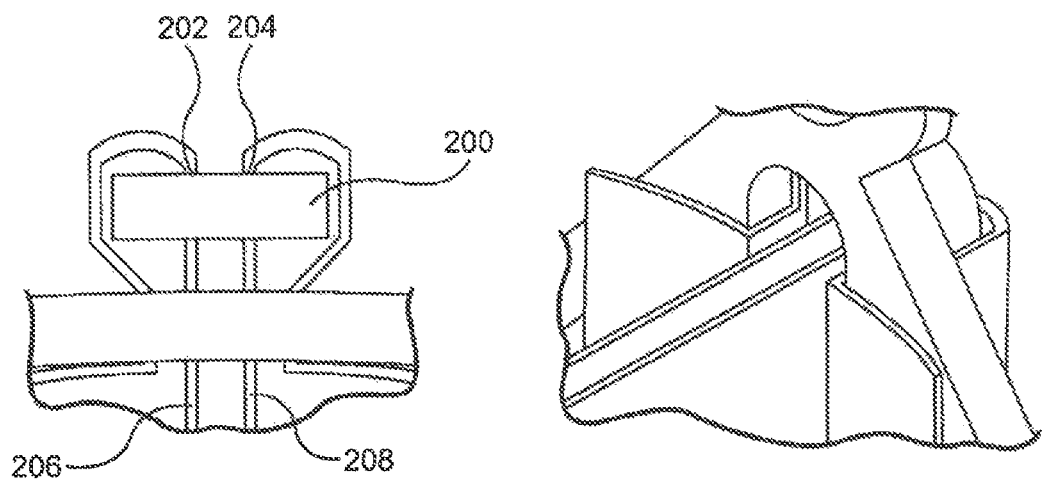
FIG. 24 is a top view of the portion of a stent, leaflets, and padded buckle mechanism illustrated in FIG. 23.
FIG. 25 is another perspective view of the portion of a stent illustrated in FIG. 23.

FIGS. 23-25 illustrate another configuration and device for the attachment of valve material to a stent structure that includes the use of a buckle member 200 that is similar in design and operation to the buckle member 180 discussed above. In this embodiment, however, the buckle member 200 includes two longitudinal slots 202, 204 that are spaced from each other across the width of the buckle member 200, rather than a single, central slot. In this way, a first leaflet 206 can be pulled through a longitudinal slot 210 in the stent and through longitudinal slot 202 of the buckle member 200, and a second leaflet 208 can be pulled through a longitudinal slot 210 in the stent and through longitudinal slot 204 of the buckle member 200. The leaflets 206, 208 can then be wrapped around the back side of the buckle member 200, pulled back through the longitudinal slot 210 in the commissure post, and pulled through the slot by a sufficient distance that the leaflets can be secured to the stent without stitching, similar to the arrangement that uses the buckle member 180.

It is noted that in many of the stent embodiments shown and described herein, the aspect ratio of certain portions of the stent can be somewhat different from that shown. Further, stent embodiments described herein may be modified to include additional structure for attachment of tissue for the valve, such as the vertical stent posts described in many of the embodiments.

Delivering any balloon-expandable stents of the invention to the implantation location can be performed percutaneously. In general terms, this includes providing a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is fluidly connected to an inflation source. It is noted that if the stent being implanted is the self-expanding type of stent, the balloon would not be needed and a sheath or other restraining means would be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly.

Prior to delivery, the stent is mounted over the balloon in a contracted state to be as small as possible without causing permanent deformation of the stent structure. As compared to the expanded state, the support structure is compressed onto itself and the balloon, thus defining a decreased inner diameter as compared to an inner diameter in the expanded state. While this description is related to the delivery of a balloon-expandable stent, the same basic procedures can also be applicable to a self-expanding stent, where the delivery system would not include a balloon, but would preferably include a sheath or some other type of configuration for maintaining the stent in a compressed condition until its deployment.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded state. Alternatively, where the support structure is formed of a shape memory material, the stent can self-expand to its expanded state.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A prosthetic valve comprising:
a stent including a central longitudinal axis and a plurality of posts extending generally parallel to the central longitudinal axis around a periphery of the stent, wherein the plurality of posts include a plurality of commissure posts and a plurality of longitudinal wires disposed between adjacent commissures posts of the plurality of commissure posts, wherein the plurality of longitudinal wires and the plurality of commissures posts are of generally equal length, wherein each of the plurality of commissure posts includes a first strut parallel to the central longitudinal axis and a second strut parallel to the central longitudinal axis, wherein the first strut and the second strut are spaced circumferentially from each other to form a longitudinal gap between the first strut and the second strut, the stent further including at least three rows of V-shaped wire structures having a first end, a second end, and a peak between the first and second ends, wherein one of the at least three rows of V-shaped wire structures is attached to a proximal-most edge of each of the commissure posts; and
a valve structure including a plurality of leaflets attached to the plurality of commissure posts,
wherein a first leaflet and an adjacent second leaflet of the plurality of leaflets extend through the longitudinal gap in a first commissure post of the plurality of commissure posts and are attached to the first commissure post.

2. The prosthetic valve of claim 1, wherein the stent further includes a longitudinal member disposed outside of the first commissure post relative to the central longitudinal axis, wherein the longitudinal member includes a longitudinal opening through which the first and second leaflets extend.

3. The prosthetic valve of claim 1,
wherein the stent further includes a longitudinal member disposed outside of the first commissure post relative to the central longitudinal axis, wherein the longitudinal member includes a longitudinal opening,
wherein the first leaflet extends through the longitudinal gap in the first commissure post away from the central longitudinal axis, extends through the longitudinal opening in the longitudinal member, wraps around the longitudinal member in a first direction, and extends back through the longitudinal gap in the first commissure post towards the central longitudinal axis, and
wherein the second leaflet extends through the longitudinal gap in the first commissure post away from the central longitudinal axis, extends to the longitudinal opening in the longitudinal member, wraps around the longitudinal member in a second direction opposite the first direction, and extends back through the longitudinal gap in the first commissure post towards the central longitudinal axis.

4. The prosthetic valve of claim 1, wherein the stent further includes a longitudinal member disposed outside of the first commissure post relative to the central longitudinal axis, wherein the longitudinal member includes a first longitudinal opening and a second longitudinal opening, wherein the first leaflet extends through first longitudinal opening and the second leaflet extends through the second longitudinal opening.

5. The prosthetic valve of claim 1,
wherein the stent further includes a longitudinal member disposed outside of the first commissure post relative to the central longitudinal axis, wherein the longitudinal member includes a first longitudinal opening and a second longitudinal opening,
wherein the first leaflet extends through the longitudinal gap in the first commissure post away from the central longitudinal axis, extends through the first longitudinal opening in the longitudinal member, wraps around the longitudinal member in a first direction, and extends back through the longitudinal gap in the first commissure post towards the central longitudinal axis, and
wherein the second leaflet extends through the longitudinal gap in the first commissure post away from the central longitudinal axis, extends through the second longitudinal opening in the longitudinal member, wraps around the longitudinal member in a second direction opposite the first direct, and extends back through the longitudinal gap in the first commissure towards the central longitudinal axis.

6. The prosthetic valve of claim 1, further comprising at least one suture attaching the first leaflet and the second leaflet to the first commissure post.

7. A prosthetic valve comprising:
a frame including a central longitudinal axis, a stent structure including a plurality of longitudinal bars, and a plurality of slot bars disposed farther from the central longitudinal axis than the stent structure is to the central longitudinal axis, wherein the longitudinal bars include a longitudinal slot disposed therethrough, wherein each of the plurality of slot bars is spaced from a corresponding longitudinal bar of the plurality of longitudinal bars such that they do not contact each other; and
a valve structure coupled to the frame, the valve structure including a plurality of leaflets;
wherein adjacent ends of a first leaflet and an adjacent second leaflet of the plurality of leaflets extend through the longitudinal slot in a first longitudinal bar of the plurality of longitudinal bars and are coupled to the first longitudinal bar.

8. The prosthetic valve of claim 7, wherein the first longitudinal bar includes a plurality of suture holes lateral of the longitudinal slot, wherein the adjacent ends of the first and second leaflets are coupled to the first longitudinal bar by sutures extending through the suture holes.

9. The prosthetic valve of claim 7, further comprising sutures attaching the adjacent ends to the first longitudinal bar.

* * * * *